United States Patent
Kruger

(10) Patent No.: US 6,633,774 B2
(45) Date of Patent: Oct. 14, 2003

(54) THERMOACOUSTIC TISSUE SCANNER

(75) Inventor: Robert A. Kruger, Indianapolis, IN (US)

(73) Assignee: Optosonics, Inc., Indianapolis, IN (US)

( * ) Notice: Subject to any disclaimer, the term of this patent is extended or adjusted under 35 U.S.C. 154(b) by 0 days.

(21) Appl. No.: 10/295,468

(22) Filed: Nov. 15, 2002

(65) Prior Publication Data

US 2003/0069491 A1 Apr. 10, 2003

Related U.S. Application Data

(62) Division of application No. 09/884,766, filed on Jun. 19, 2001.

(51) Int. Cl.[7] .............................................. A61B 5/05
(52) U.S. Cl. ..................................................... 600/407
(58) Field of Search ........................ 600/407, 438–437; 250/363.61; 606/2, 20, 27, 32; 374/6, 7

(56) References Cited

U.S. PATENT DOCUMENTS

| | | | | |
|---|---|---|---|---|
| 3,603,303 A | 9/1971 | Stouffer | ....................... | 128/2 R |
| 4,059,010 A | 11/1977 | Sachs | ........................... | 73/596 |
| 4,206,763 A | 6/1980 | Pedersen | .................... | 128/660 |
| 4,222,274 A | 9/1980 | Johnson | ........................ | 73/607 |

(List continued on next page.)

FOREIGN PATENT DOCUMENTS

| | | | | |
|---|---|---|---|---|
| DE | 26 43 126 | 3/1977 | .......... | G01N/29/00 |
| DE | 39 25 312 | 4/1990 | .......... | G03B/42/00 |
| DE | 44 46 390 | 7/1996 | .......... | G01N/21/25 |
| EP | 0 018 771 | 4/1980 | .......... | A61B/10/00 |
| EP | 0 318 283 | 5/1989 | .......... | G01N/29/04 |
| EP | 0 582 384 | 7/1992 | .......... | G01N/21/17 |
| WO | 83/00009 | 1/1983 | .......... | A61B/10/00 |
| WO | WO97/41418 | 11/1997 | .......... | G01N/21/00 |
| WO | WO99/30620 | 6/1999 | .......... | A61B/8/13 |
| WO | WO00/19243 | 4/2000 | .......... | G01V/3/08 |
| WO | WO00/19244 | 4/2000 | .......... | G01V/3/08 |
| WO | WO00/22987 | 4/2000 | .......... | A61B/8/00 |

OTHER PUBLICATIONS

Kruger et al., *Photoacoustic ultrasound (PAUS)—Reconstruction tomography*, Med. Phys. 22 (10), Oct. 1995, pp. 1605–1609.

Liu et al., *Simulation of Photoacoustic Signal Production in Human Breast Phantoms at 1064 nm*, SPIE vol. 2708, 1996, pp. 312–322.

(List continued on next page.)

*Primary Examiner*—Daniel Robinson
(74) *Attorney, Agent, or Firm*—Wood, Herron & Evans, L.L.P.

(57) ABSTRACT

A thermoacoustic imaging system including an electromagnetic radiation source for irradiating said tissue to stimulate a thermoacoustic response, a coupling media for acoustically coupling the response to an acoustic sensor array, and an acoustic sensor array. The array comprises sensors arranged on a surface, which is rotatable about an axis to position said sensors in a plurality of positions for detecting the thermoacoustic response. The angular extent of the surface about the axis, subtends an angle that is less than a full revolution, streamlining the device and permitting flexibility in positioning the radiation source and other elements of the device. The source of electromagnetic radiation for irradiating the tissue is a plurality of sources arranged about the tissue and producing synchronized electromagnetic radiation in varying polarizations or phases to irradiate said tissue with electromagnetic radiation of a desired polarization. A thermoacoustic imaging system sized to be held within the human hand is also disclosed.

6 Claims, 6 Drawing Sheets

U.S. PATENT DOCUMENTS

| | | | | |
|---|---|---|---|---|
| 4,233,988 A | | 11/1980 | Dick et al. ................... | 128/660 |
| 4,246,784 A | | 1/1981 | Bowen ...................... | 73/339 A |
| 4,255,971 A | | 3/1981 | Rosencwaig ................ | 73/606 |
| 4,267,732 A | | 5/1981 | Quate ......................... | 73/606 |
| 4,385,634 A | * | 5/1983 | Bowen ....................... | 600/407 |
| 4,481,821 A | | 11/1984 | Chamuel ..................... | 73/617 |
| 4,484,820 A | | 11/1984 | Rosencwaig .................. | 374/6 |
| 4,485,819 A | | 12/1984 | Igl ............................. | 128/660 |
| 4,509,368 A | | 4/1985 | Whiting et al. ............... | 73/624 |
| 4,545,385 A | | 10/1985 | Pirschel ...................... | 128/660 |
| 4,681,120 A | | 7/1987 | Kunii ......................... | 128/660 |
| 4,874,251 A | | 10/1989 | Thomas et al. ............... | 374/45 |
| 4,950,897 A | | 8/1990 | Mandelis et al. ........... | 250/334 |
| 5,070,733 A | * | 12/1991 | Nagata et al. ................ | 73/602 |
| 5,170,666 A | | 12/1992 | Larsen ........................ | 73/571 |
| 5,348,002 A | | 9/1994 | Caro .......................... | 128/633 |
| 5,402,786 A | | 4/1995 | Drummond .............. | 128/653.2 |
| 5,615,675 A | | 4/1997 | O'Donnell et al. ...... | 128/653.1 |
| 5,657,754 A | | 8/1997 | Rosencwaig ................ | 128/633 |
| 5,713,356 A | | 2/1998 | Kruger ..................... | 128/653.1 |
| 5,800,350 A | | 9/1998 | Coppleson et al. .......... | 600/372 |
| 5,840,023 A | | 11/1998 | Oraevsky et al. ........... | 600/407 |
| 5,865,743 A | | 2/1999 | Godik ......................... | 600/407 |
| 5,941,821 A | * | 8/1999 | Chou .......................... | 600/316 |
| 6,002,958 A | | 12/1999 | Godik .................... | 250/339.11 |
| 6,102,857 A | | 8/2000 | Kruger ........................ | 600/437 |
| 6,104,942 A | | 8/2000 | Kruger ........................ | 600/407 |
| 6,192,262 B1 | | 2/2001 | Godik ......................... | 600/407 |
| 6,216,025 B1 | | 4/2001 | Kruger ........................ | 600/407 |
| 6,405,069 B1 | * | 6/2002 | Oraevsky et al. ........... | 600/407 |

OTHER PUBLICATIONS

Chen et al., *A new laser–ultrasound transducer for medical applications*, Ultrasonics vol. 32, No. 4 (1994) 309–313.

Appledorn et al., *Energy Deposition Patterns in the Breast at 1064 nm for Photoacoustic Ultrasound*, SPIE vol. 2708 (1996) 655–664.

Fang et al., *Microwave Applicators for Photoacoustic Ultrasonography*, SPIE vol. 2708 (1996) 645–654.

Beard et al., *Characterization of post mortem arterial tissue using time–resolved photoacoustic spectrosopy at 436, 461 and 532 nm*, Phys. Med. Biol. 42 (1997) 177–198.

Shan et al., *Modeling of a photoacoustic probe designed for medical applications*, Ultrasonics 34 (1996) 575–577.

Ossoff et al., *Computer–Assisted Surgical Techniques: A Vision for a Future of Otolaryngology—Head and Neck Surgery*, Jrnl of Otolaryngology, vol. 23, No. 5 (1994) 354–359.

Hunter et al., *Acoustic signals of nonthermal origin from high energy protons in water*, J. Acoust. Soc. Am. 69(9), 1557–1562, Jun. 1981.

Bowen, *Acoustic Radiation Temperature of Non–Invasive Thermometry*, Automedica, vol. 8, 247–267, 1987.

Hebden et al., *Tomographic Imaging Using Picosecond Pulses of Light*, SPIE vol. 1443, Medical Imaging V: Image Physics 294–300, 1991.

Nasoni et al., *Thermoacoustic Emission by Deeply Penetrating Microwave Radiation*, Poc. of IEEE Ultrasonic Symposium, 633–38, 1984.

Bowen et al., *Some Experimental Results of the Thermoacoustic Imaging of Tissue Equivalent Phantom Materials*, Proc. of IEEE Ultrasonic Symposium 2: 823–27, 1981.

Bowen, *Radiation–Induced Thermoacoustic Soft Tissue Imaging*, Proc. of IEEE Ultrasonic Symposium 2: 817–822, Jun., 1981.

Kruger, *Photo–acoustic ultrasound*, Med. Phys. 21(1): 127–131, 1994.

Kruger et al., *Photoacoustic ultrasound: pulse production and detection of 0.5* liposyn, Med. Phys. 21(7): 1179–1184, 1994.

Kruger et al., *Photoacoustic Ultrasound: Theory and Experimental Results*, SPIE vol. 2134A: 114–121, 1994.

* cited by examiner

THERMOACOUSTIC TISSUE SCANNER

This is a divisional of application Ser. No. 09/884,766, filed Jun. 19, 2001.

This application is related to application Ser. No. 009/243,004 filed Feb. 2, 1999, entitled THERMOACOUSTIC COMPUTED TOMOGRAPHY SCANNER, now U.S. Pat. No. 6,216,025, which is a divisional application of Ser. No. 09/076,385 filed May 12,1998, now U.S. Pat. No. 6,104,942, and copending application Ser. No. 09/076,968 filed May 13, 1998, now U.S. Pat. No. 6,102,857, which is a divisional of Patent Cooperation Treaty application designating the Ser. No. 97/17832, filed Oct. 1, 1997, which is a continuation of application Ser. No. 08/719,736, filed Oct. 4, 1996, now U.S. Pat. No. 5,713,356, issued Feb. 3, 1998, all of the foregoing being filed in the name of the same assignee as the present application and assigned to the same assignee as the present application , and all of the foregoing hereby incorporated by reference into this application.

FIELD OF THE INVENTION

The present invention relates to imaging properties of tissue based upon differential absorption of electromagnetic waves in differing tissue types by photo-acoustic techniques.

BACKGROUND OF THE INVENTION

It is well established that different biologic tissues display significantly different interactions with electromagnetic radiation from the visible and infrared into the microwave region of the electromagnetic spectrum. While researchers have successfully quantified these interactions in vitro, they have met with only limited success when attempting to localize sites of optical interactions in vivo. Consequently, in vivo imaging of disease at these energies has not developed into a clinically significant diagnostic tool.

In the visible and near-infrared regions of the electromagnetic spectrum, ubiquitous scattering of light presents the greatest obstacle to imaging. In these regions, scattering coefficients of 10–100 $mm^{-1}$ are encountered. Consequently, useful numbers of unscattered photons do not pass through more than a few millimeters of tissue, and image reconstruction must rely on multiply-scattered photons. While efforts persist to use visible and infrared radiation for imaging through thick tissue (thicker than a few centimeters), clinically viable imaging instrumentation has not been forthcoming.

In the microwave region (100–3000 MHZ), the situation is different. Scattering is not as important, since the wavelength (in biologic tissue) at these frequencies is much greater than the "typical" dimension of tissue inhomogeneities ($\approx 1$ $\mu m$). However, the offsetting effects of diffraction and absorption have forced the use of long wavelengths, limiting the spatial resolution that can be achieved in biologic systems. At the low end of the microwave frequency range, tissue penetration is good, but the wavelengths are large. At the high end of this range, where wavelengths are shorter, tissue penetration is poor. To achieve sufficient energy transmission, microwave wavelengths of roughly 2–12 cm (in tissue) have been used. However, at such a long wavelength, the spatial resolution that can be achieved is no better than roughly ½ the microwave length, or about 1–6 cm.

In vivo imaging has also been performed using ultrasound techniques. In this technique, an acoustic rather than electromagnetic wave propagates through the tissue, reflecting from tissue boundary regions where there are changes in acoustic impedance. Typically, a piezoelectric ceramic chip is electrically pulsed, causing the chip to mechanically oscillate at a frequency of a few megahertz. The vibrating chip is placed in contact with tissue, generating a narrow beam of acoustic waves in the tissue. Reflections of this wave cause the chip to vibrate, which vibrations are converted to detectable electrical energy, which is recorded.

The duration in time between the original pulse and its reflection is roughly proportional to the distance from the piezoelectric chip to the tissue discontinuity. Furthermore, since the ultrasonic energy is emitted in a narrow beam, the recorded echoes identify features only along a narrow strip in the tissue. Thus, by varying the direction of the ultrasonic pulse propagation, multi-dimensional images can be assembled a line at a time, each line representing the variation of acoustic properties of tissue along the direction of propagation of one ultrasonic pulse.

For most diagnostic applications, ultrasonic techniques can localize tissue discontinuities to within about a millimeter. Thus, ultrasound techniques are capable of higher spatial resolution than microwave imaging.

The photoacoustic effect was first described in 1881 by Alexander Graham Bell and others, who studied the acoustic signals that were produced whenever a gas in an enclosed cell is illuminated with a periodically modulated light source. When the light source is modulated at an audio frequency, the periodic heating and cooling of the gas sample produced an acoustic signal in the audible range that could be detected with a microphone. Since that time, the photoacoustic effect has been studied extensively and used mainly for spectroscopic analysis of gases, liquid and solid samples.

It was first suggested that photoacoustics, also known as thermoacoustics, could be used to interrogate living tissue in 1981, but no subsequent imaging techniques were developed. The state of prior art of imaging of soft tissues using photoacoustic, or thermoacoustic, interactions is best summarized in Bowen U.S. Pat. No. 4,385,634. In this document, Bowen teaches that ultrasonic signals can be induced in soft tissue whenever pulsed radiation is absorbed within the tissue, and that these ultrasonic signals can be detected by a transducer placed outside the body. Bowen derives a relationship (Bowen's equation 21) between the pressure signals p(z,t) induced by the photoacoustic interaction and the first time derivative of a heating functions, S(z,t), that represents the local heating produced by radiation absorption. Bowen teaches that the distance between a site of radiation absorption within soft tissue is related to the time delay between the time when the radiation was absorbed and when the acoustic wave was detected.

Bowen discusses producing "images" indicating the composition of a structure, and detecting pressure signals at multiple locations, but the geometry and distribution of multiple transducers, the means for coupling these transducers to the soft tissue, and their geometrical relationship to the source of radiation, are not described. Additionally, nowhere does Bowen teach how the measured pressure signals from these multiple locations are to be processed in order to form a 2- or 3-dimensional image of the internal structures of the soft tissue. The only examples presented are 1-dimensional in nature, and merely illustrate the simple relationship between delay time and distance from transducer to absorption site.

The above-referenced U.S. Pat. No. 5,713,356, filed by the present inventor, details a diagnostic imaging technique in which pulses of electromagnetic radiation are used to excite a relatively large volume of tissue and stimulate acoustic energy. Typically, a large number of such pulses (e.g., 100 to 100,000), spaced at a repetition interval, are generated to stimulate the tissue. The above-referenced U.S. Pat. No. 5,713,356 discloses methods for measuring the relative time delays of the acoustic waves generated by a sequence of such pulses, and for converting these time delays into a diagnostic image.

SUMMARY OF THE INVENTION

In one aspect, the invention features a thermoacoustic imaging system including an electromagnetic radiation source for irradiating said tissue to stimulate a thermoacoustic response, a coupling media for acoustically coupling the response to an acoustic sensor array, and an acoustic sensor array. The array comprises sensors arranged on a surface, which is rotatable about an axis to position said sensors in a plurality of positions for detecting the thermoacoustic response. The angular extent of the surface about the axis, subtends an angle that is less than a full revolution, so that the surface is substantially smaller than the sensor bowl described in the above-referenced U.S. Pat. No. 5,713,356, streamlining the device and permitting greater flexibility in positioning the radiation source and other elements of the device.

In the described specific embodiment, the array surface is made of a plurality of flat sections, in an arc, arranged such that a geometric center of each section is equidistant from a common point on the axis of rotation. Each section each carries a plurality of acoustic sensors, the sections nearer to the axis of rotation carrying fewer acoustic sensors than the sections further from that axis.

The acoustic sensors may comprise singe piezoelectric sensors, or dual sensors arranged side-by-side or coaxially with a combiner for combining their signals to form a combined signal.

A sensor array such as described may also be used, in conjunction with an ultrasound beam steering circuit, as an ultrasonic imaging device. Specifically, the beam steering circuit is coupled to the acoustic sensors and stimulates the sensors to produce an ultrasound beam directed into said tissue. Echoes of this beam are received by the sensors and combined to form an image of the tissue.

In a second aspect, the invention features a thermoacoustic imaging system, in which the source of electromagnetic radiation for irradiating the tissue is a plurality of sources arranged about the tissue and producing synchronized electromagnetic radiation in varying polarizations or phases to irradiate said tissue with electromagnetic radiation of a desired polarization.

In the described specific embodiment, the sources comprise waveguides positioned to launch electromagnetic radiation toward said tissue, in varying polarizations or phases, such as vertical and horizontal polarization and/or relative phase shifts of zero and ninety degrees.

In a further aspect, the invention features a handheld thermoacoustic imaging system for imaging structures of tissue. Specifically, thermoacoustic imaging is performed with a device sized to be held within the human hand, which has a source of electromagnetic radiation for irradiating the tissue to stimulate a thermoacoustic response, and an acoustic sensor array for detecting the thermoacoustic response.

The above and other objects and advantages of the present invention shall be made apparent from the accompanying drawings and the description thereof.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

FIG. 4A-1 is an illustration of a first embodiment of a dual acoustic sensor, and FIG. 4A-2 is an illustration of a second embodiment of a dual acoustic sensor;

FIGS. 6A, 6B, 6C, 6D, 6E-1 and 6E-2 are illustrations of configurations of polarization and phase applied to the waveguide array of FIG. 1 to achieve alternative polarizations of the radiation in a breast using the system of FIG. 1.

DETAILED DESCRIPTION OF SPECIFIC EMBODIMENTS

Figure 1:
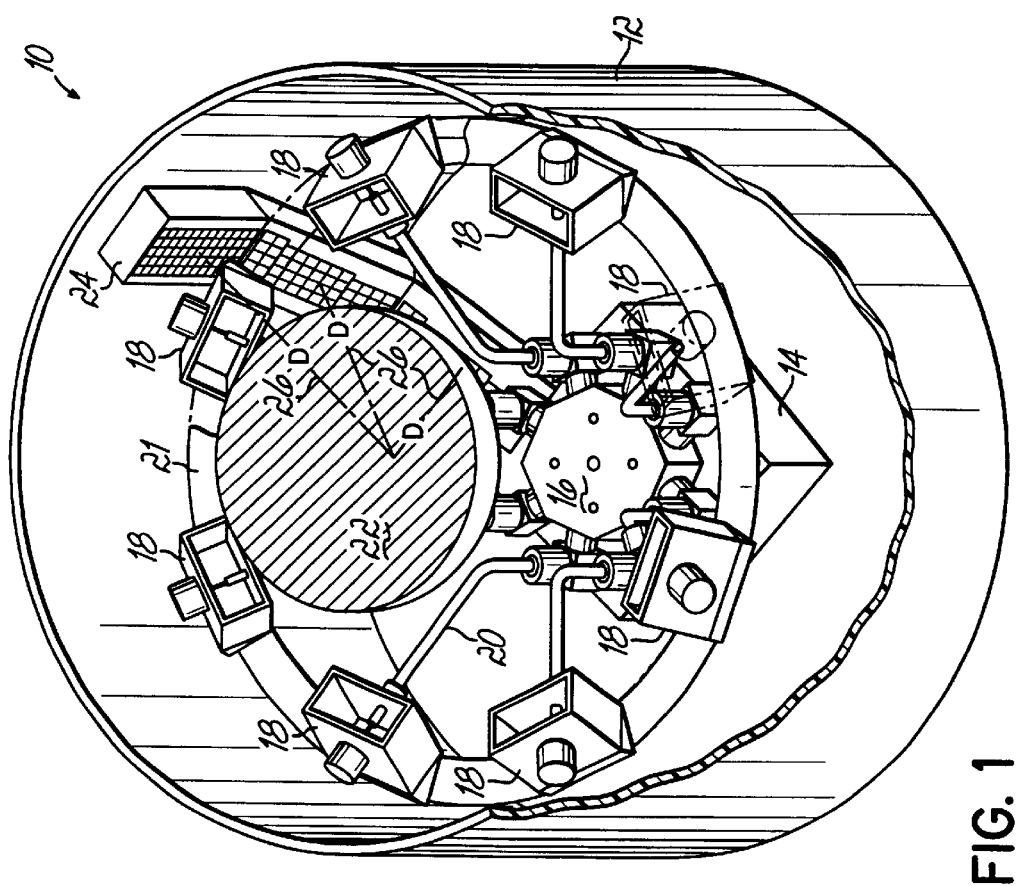
FIG. 1 is a perspective view of a thermoacoustic computed tomography system.

FIG. 1 illustrates the structure of a thermoacoustic computed tomography (TACT) system in accordance with one embodiment of the present invention. In the embodiment 10 shown in FIG. 1, a tank 12 is filled with an acoustic coupling media such as distilled and deionized water. Tank 12 has a cylindrical shape and includes in its interior, immersed in the coupling media, a rotary stage 14 supporting an electromagnetic radiation system as well as an acoustic sensor. As described in the above-referenced U.S. Pat. No. 5,713,356, the electromagnetic radiation system is used to stimulate a thermoacoustic response within tissue, which thermoacoustic response is detected by the acoustic sensor.

More specifically, the electromagnetic radiation system comprises an electromagnetic splitter 16 for dividing electromagnetic energy from an external source for delivery to each of eight waveguides 18. Electromagnetic radiation is carried to waveguides 18 by coaxial conductors 20 associate with each waveguide 18, and connecting the waveguide 18 to splitter 16. An external positioning ring 21 connects to the lower surface of each waveguide 18 to maintain the relative position of each waveguide 18 within tank 12. Waveguides 18 are positioned annularly about the central area of tank 12 so as to irradiate a human breast 22 positioned in the central area of tank 12. Waveguides 18 are positioned below the upper surface of tank 12 and angled upwardly toward the central area of tank 12 so as to produce relatively uniform irradiation of the breast 22.

Also positioned within tank 12 is a detector array 24 carrying a plurality of piezoelectric or other forms of acoustic sensors for detecting thermoacoustic signals produced within the tissue of the breast 22 in response to electromagnetic radiation emitted by the waveguides 18. The detector array 24 subtends a small angle around the entire circumference of the tank 12. By rotation of the rotary stage 14, waveguides 18 and detector array 24 may be rotated to a plurality of rotational positions to thereby collect thermoacoustic signals produced in each angular direction from the breast 22 under irradiation of electromagnetic radiation from waveguide 18. The resulting thermoacoustic signals collected at a plurality of positions surrounding the breast 22 can then be used in a reconstruction algorithm such as described in the above-referenced U.S. Pat. No. 5,713,356, to produce thermoacoustic images.

Figure 2:
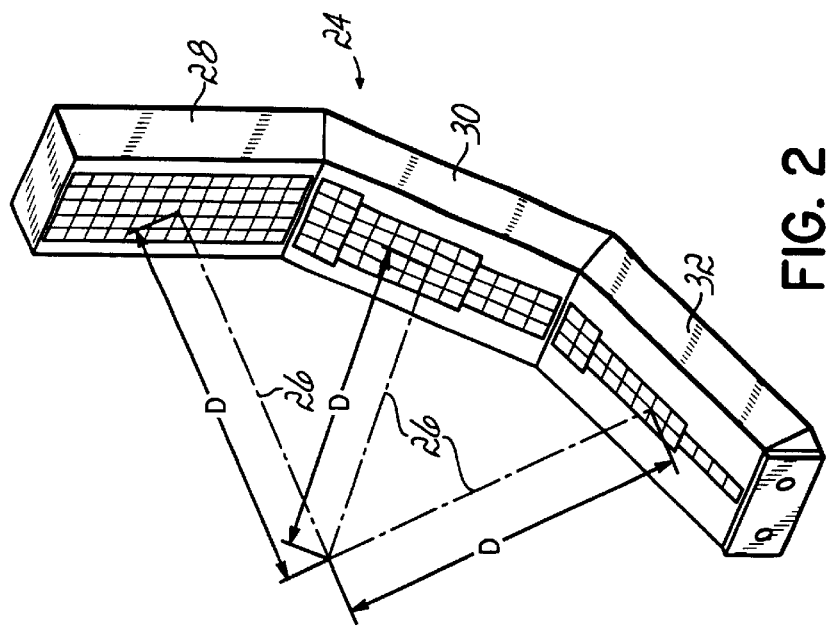
FIG. 2 is a view of the sector scanner of the system of FIG. 1.

Referring now to FIG. 2, details of the detector array 24 can be explained. The array is comprised of three flat-faced subarrays 28, 30 and 32, each of which subtends an angle of 11.25° relative to the central axis of the tank 12. The array is formed of three flat sections 28, 30 and 32 to simplify manufacturing, however the array could also be formed of a smoothly curved hemispherical section subtending a similar angular portion about the axis of the cylindrical tank 12. In use, the array is rotated 11.25° between each data acquisition to each of 32 discrete positions about the vertical axis of tank 12, which positions span a full 360° about this axis. The sections 28, 30 and 32 are positioned such that geometric center of each section is equidistant from a common point, as illustrated by line segments 26. The common point is centralized within the breast when immersed within tank 12, and preferably on the central axis of cylindrical tank 12.

Figure 3:
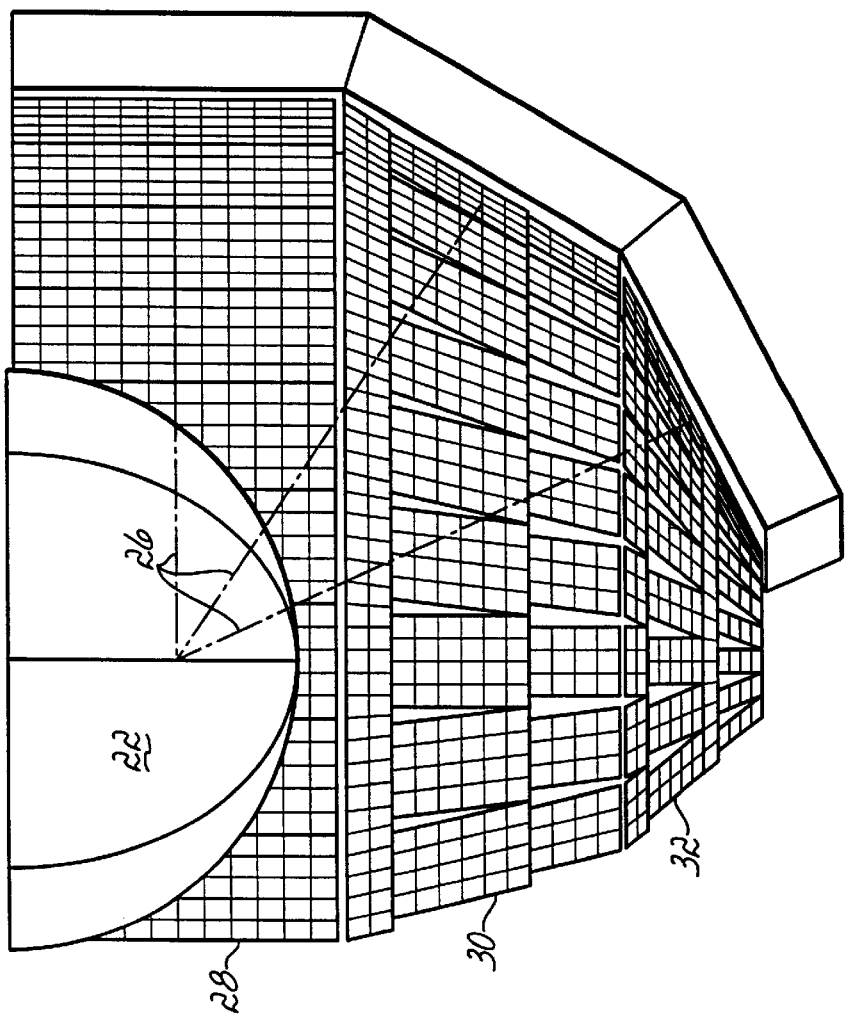
FIG. 3 is a diagram of the sensor positions achieved during rotation of the scanner of FIG. 2.

Referring to FIG. 3, the relative positions of the transducers of the transducer array, as the array is rotated in 11.25° increments, can be appreciated. Nine discrete positions of the array are illustrated in FIG. 3, corresponding to one-quarter revolution, or 90° of rotation of the array about the breast 22. It can be appreciated from FIG. 3 that the resulting transducer positions are evenly distributed across the resulting hemispherical surface surrounding the breast 22, as is desirable for reconstruction.

The detector array illustrated in FIGS. 1–3 has a variety of potential advantages over the hemispherical bowl array illustrated in the above-referenced U.S. Pat. No. 5,713,356. Specifically, the spacing of the acoustic detector locations is more nearly uniform over the surface of a hemisphere using a detector array such as illustrated in FIGS. 1–3. Also, the detector array is more compact and allows flexibility of the location and distribution of RF emitting elements around the breast, as compared to a hemispherical bowl sensor. Finally, the detector array may be less expensive to manufacture owing to its less complex mechanical structure as compared to a hemispherical bowl as shown in the above-referenced U.S. Pat. No. 5,713,356.

Figures 1, 4A:
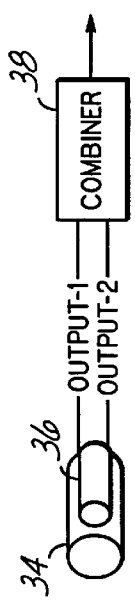
Figures 2, 4A:
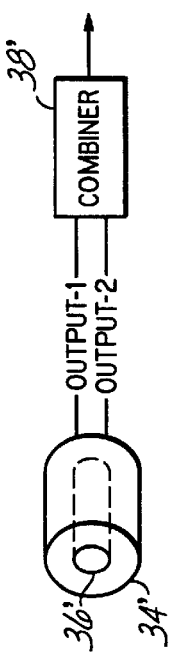

Referring now to FIG. 4A-1 and FIG. 4A-2, possible structures for the transducers within the detector array can be explained. In one embodiment, the acoustic sensors and the detector array comprise single piezoelectric elements chosen for their acoustic properties to match to the frequency ranges expected to be produced by the thermoacoustic effect used under the present invention. In an alternative embodiment, where a particularly broad acoustic bandwidth is desirable, each acoustic sensor in the detector array may be comprised of two or more discrete acoustic sensors, such as two discrete piezoelectric elements, which collectively are used as an acoustic sensor. As illustrated in FIG. 4A-1, a first sensor 34 and a second sensor 36 may be positioned physically adjacent at each detector sensor site, and the signals from these sensors may be delivered to a signal combiner 38 to produce a combined output signal. Alternatively, as illustrated in FIG. 4A-2, a first acoustic sensor 34' may be positioned coaxially surrounding a second acoustic sensor 36', and the two output signals from each sensor are again delivered to a combiner 38' to produce a single signal representing the output of the sensor. It will be appreciated that piezoelectric sensors and other forms of acoustic sensors may have different physical geometries to correspond to different frequency response characteristics that may be desired for acoustic sensors. These different physical geometries may permit adjacent positioning of sensors as shown in FIG. 4A-1, or permit concentric positioning of sensors as shown in FIG. 4A-2.

Figure 4B:
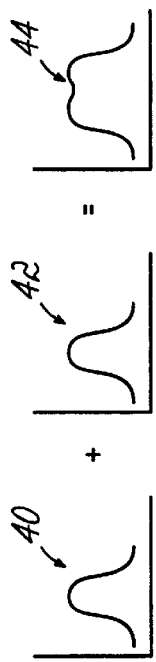
FIG. 4B is an illustration of the combination of frequency response characteristics of two acoustic sensors.

Referring to FIG. 4B, it can be seen that through the use of a combiner such as 38 or 38' the frequency response characteristic of multiple sensors may be combined to advantageously produce a frequency response characteristic of a more broadband nature as may be needed for TACT imaging. As illustrated in FIG. 4B, a first frequency response characteristic 40 having a relatively lower frequency band of response is combined with a second frequency response characteristic 42 having a relatively higher band response to produce a combined response 44 having broader bandwidth than either of the response curves from which it is created.

Figure 5:
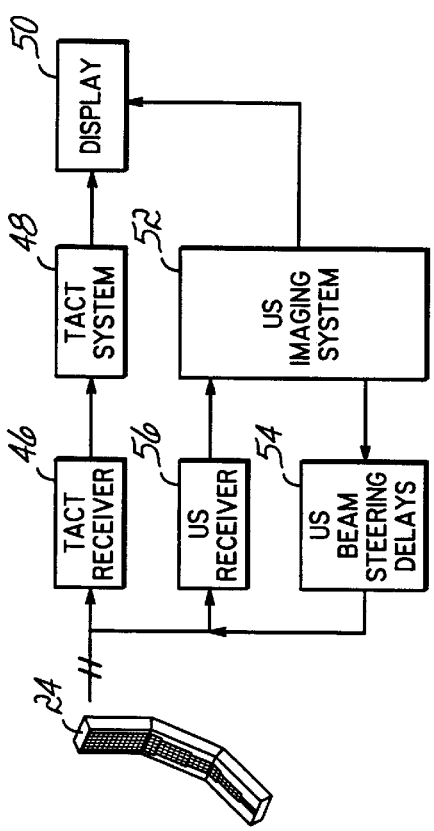
FIG. 5 is an illustration of the electronic circuitry used in a combination TACT and ultrasound imaging system using the scanner of FIG. 2.

Referring now to FIG. 5, the use of detector array 24 in TACT imaging as well as ultrasonic imaging can be explained. A further advantage of detector array 24 is that it provides an array of adjacent acoustic sensors that may also be used in a conventional ultrasound process for ultrasound imaging of the breast tissue in conjunction with or in addition to thermoacoustic imaging. Specifically, the acoustic sensors in detector array 24 are coupled to a TACT receiver 46 and to a TACT processing system 48 for producing TACT images using acoustic signals detected by the detector array 24. Details of this process are described in the above-referenced U.S. Pat. No. 5,713,356, and are not repeated here. The resulting TACT-generated image may be displayed on a display for diagnostic purposes. Simultaneously, or as a separate imaging modality, the sensors on array 24 may be used for conventional ultrasound imaging of the subject tissue. Specifically, for this application, an ultrasound beam steering delay circuit 54 is controlled by an ultrasound imaging system 52 to produce a narrow sweeping beam of ultrasound directed from the piezoelectric elements of detector array 24 into the tissue of the breast. Echoes produced within the breast are then received by the acoustic sensors in detector array 24 and delivered to an ultrasound receiver 56, and then relayed to the ultrasound imaging system 52 using conventional ultrasound imaging techniques. As a result, an ultrasound image of the tissue may be created and presented on display 50 overlaid with or as a substitute for comparison to the TACT-generated image produced by the TACT system 48. Combined ultrasound and TACT imaging created in this manner may serve diagnostic purposes that cannot be realized by either modality alone, by permitting discrimination of tissue structures that are more readily recognized with each modality, and permitting direct comparison of images produced by each modality by a clinician operating the scanning system and viewing display 50.

Referring now to FIGS. 6A–6E-2, the use of the waveguides 18 in creating polarized electromagnetic radiation within the breast can be explained. The polarization of electromagnetic radiation irradiating the breast may affect the image produced. Specifically, polarization refers to the axes of oscillation of magnetic and electric field in electromagnetic radiation, and therefore relates to the direction in which tissue is stimulated by electromagnetic radiation to produce thermoacoustic effects. Different polarization directions may, therefore, produce different thermoacoustic reactions within tissue. Waveguide structures 18 can be manipulated to change the polarization of radiation in the breast, and such changes may be useful in manipulating the generated image to produce enhanced images of structures of interest. For example, tissue structures that are elongated may be better imaged by polarization that is either aligned with or perpendicular to the elongated dimension of those structures.

Figure 6A:
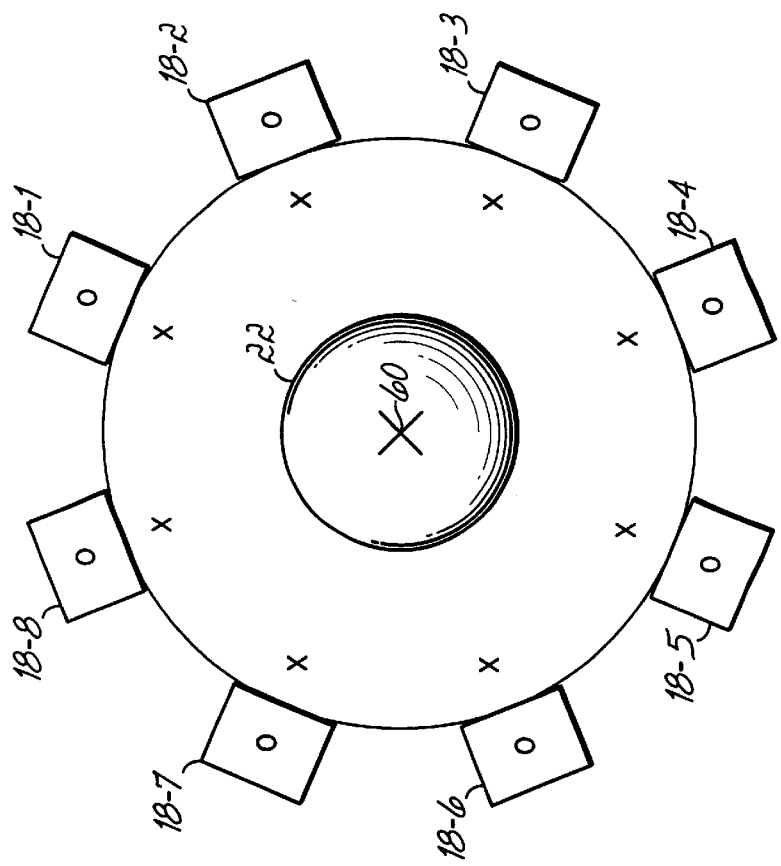

FIGS. 6A–6E-2 are plan views of the thermoacoustic computed tomography scanning apparatus illustrated in FIG. 1. The interior ends of each of the waveguides 18-1–18-8 are shown schematically, as is the breast tissue 22 being imaged. As seen in FIG. 6A, polarization directed vertically downward (into the paper as shown in FIG. 6A) can be generated by orienting the polarization of radiation emitted from each of the waveguides 18 to be also vertically downward (also into the paper as shown in FIG. 6A).

Figure 6C:
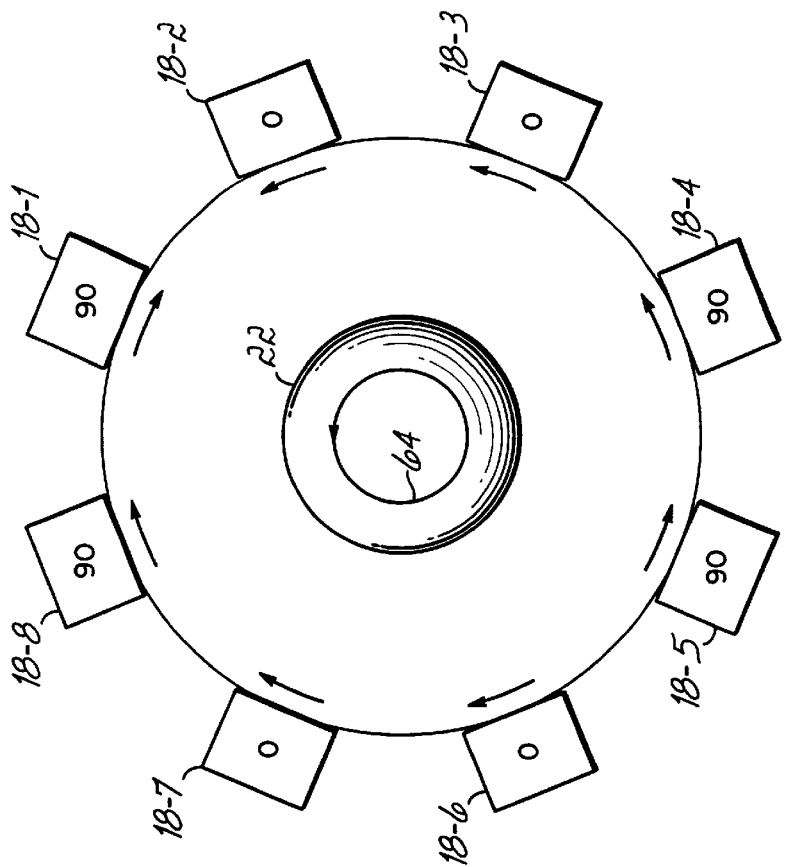
Figure 6B:
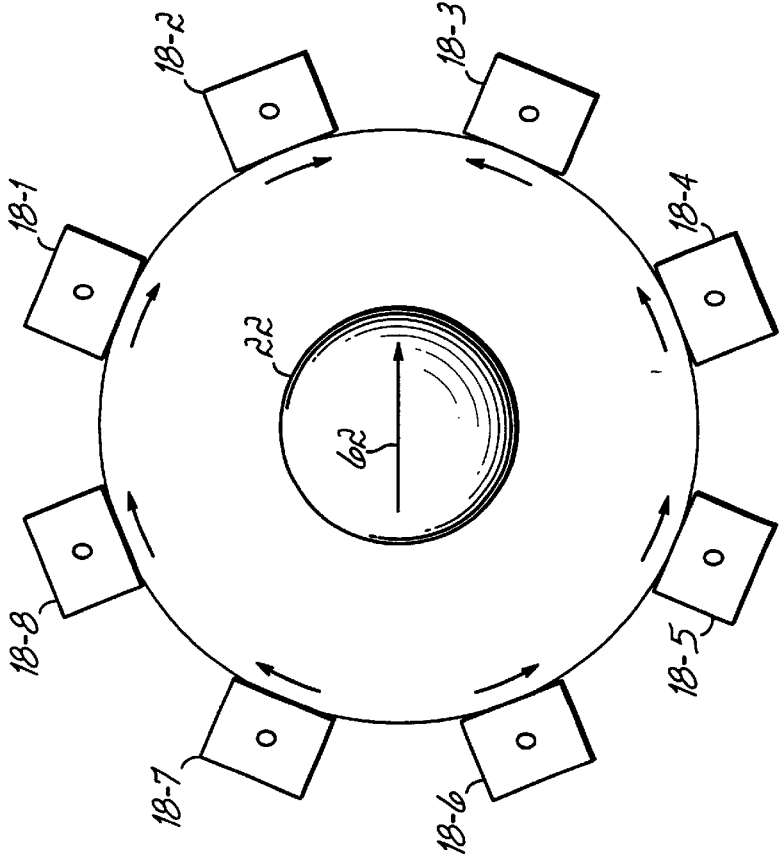

As seen in FIG. 6B, polarization that is horizontal (across the paper as shown in FIG. 6A) can be created by producing horizontal polarization at each of the waveguides 18 in the directions illustrated adjacent to each waveguide.

Referring to FIG. 6C, horizontal circular polarization 64 may be produced in the tissue by appropriate polarization and phase delays to the waveguides 18. Specifically, 90° phase delays are applied to radiation emitted by waveguides 18-1, 18-4, 18-5 and 18-8. Horizontal polarization is provided by each of the waveguides as shown in FIG. 6C in the direction shown in FIG. 6C.

Figures 1, 6E:
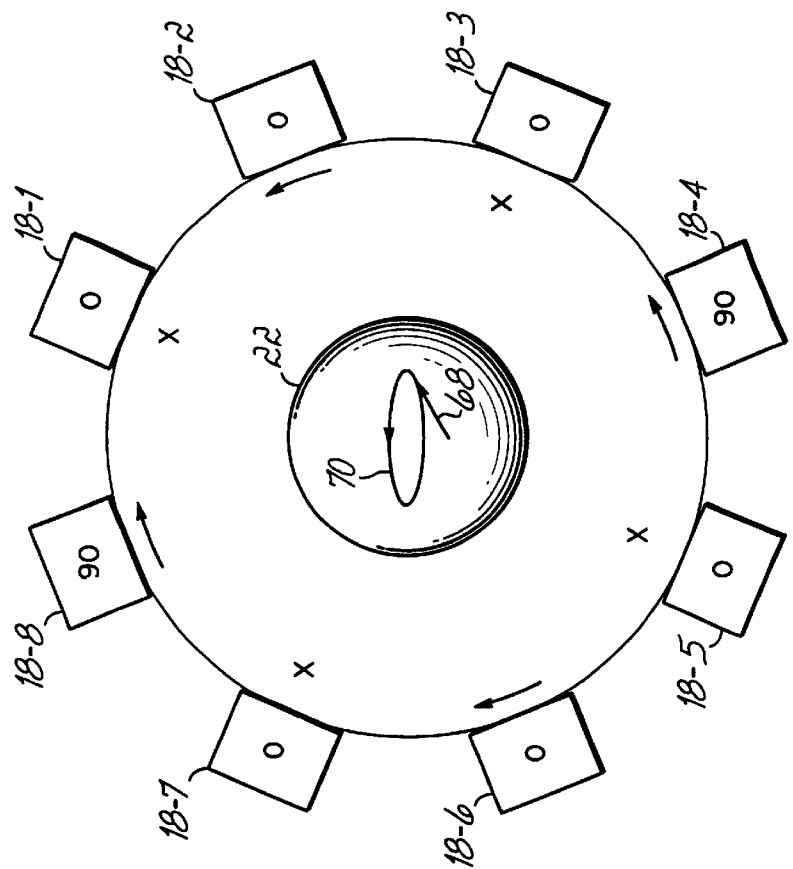
Figure 6D:
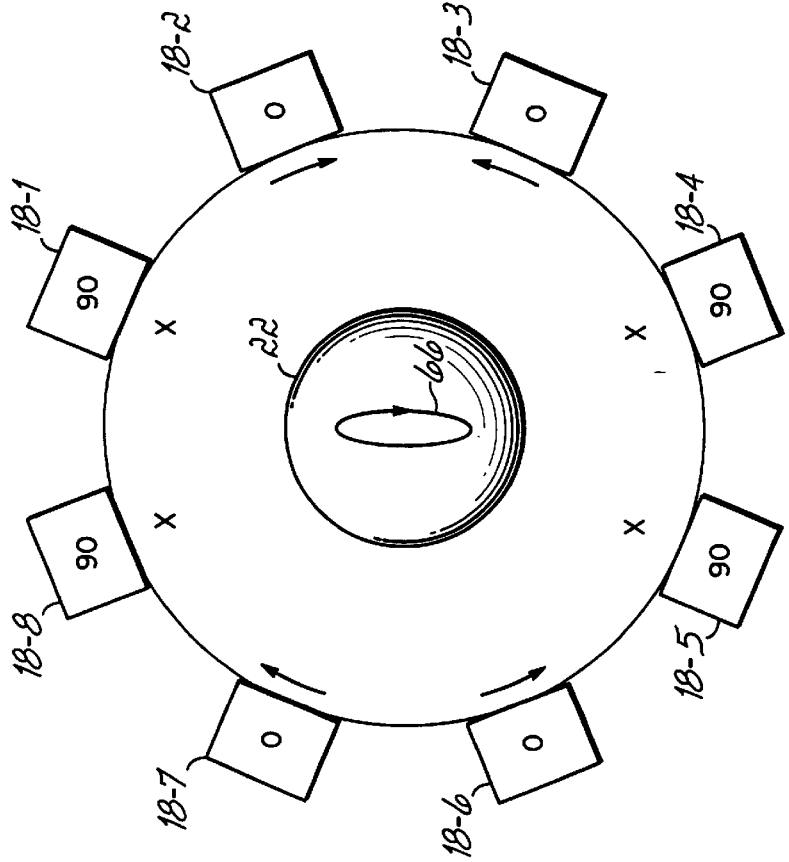

As seen in FIG. 6D, vertical circular polarization may be achieved through alternative phase delay and polarization arrangements shown in FIG. 6D. Here again, 90° phase delays are applied to radiation emitted from waveguides 18-1, 18-4, 18-5 and 18-8. Horizontal and vertical polarization is produced by the waveguides in the directions illustrated in FIG. 6D.

Referring to FIG. 6E-1, vertically precessing electrical field may be generated in the breast tissue 22 by an appropriate arrangement of polarizations and phase delays as shown in FIG. 6E-1. Specifically, 90° phase delays are applied to the electromagnetic radiation emitted from waveguides 18-4 and 18-8, and alternating horizontal and vertical polarization are applied to the waveguides as illustrated in FIG. 6E-1. The resulting electric field has a vertical component 68 which precesses about a circular path 70 as illustrated in FIG. 6E-1. FIG. 6E-2 provides a side view of breast tissue 22 exposed to vertical precessing electric field, showing that the direction of the electric field 68 is at an angle of 35° 72 from vertical and precesses about circular path 70 at this angle.

Figure 7:
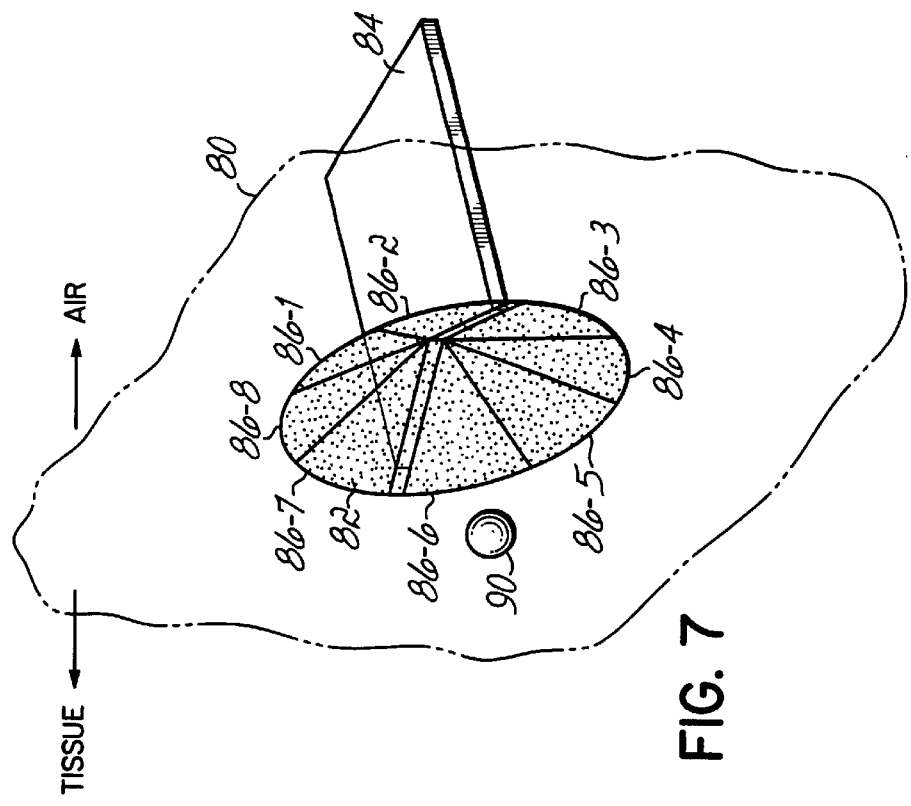
FIG. 7 is an illustration of a hand-held TACT scanner.
Figures 2, 6E:
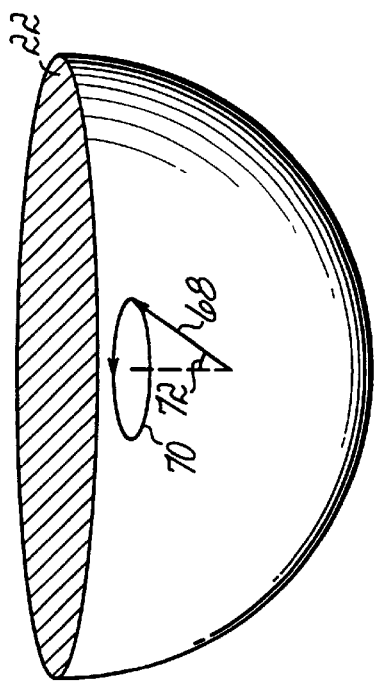

FIG. 7 illustrates a handheld TACT scanner. This scanner is placed in physical contact with the surface 80 of the skin of a patient to image tissue structures directly beneath the skin, such as a tumor or suspicious mass 90. A membrane 82 on the outer surface of the scanner is pressed against the skin surface 80 to achieve good acoustic coupling thereto. The scanner utilizes a waveguide 84 for launching electromagnetic radiation into the tissue to stimulate a thermoacoustic response. Resulting thermoacoustic signals are received by a plurality of acoustic sensors 86-1 through 86-8 arranged about the periphery of the handheld scanner. An acoustic coupling media such as a water soluble gel is contained between membrane 82 and sensors 86-1 through 86-8 to achieve good acoustic coupling from the tissue to the sensors. In use, thermoacoustic responses produced in the tissue and received by sensors 86-1 through 86-8 are back projected in the manner described in the above-referenced U.S. Pat. No. 5,713,356, to form an image of the tissue structures beneath the skin such as the mass 90.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A thermoacoustic imaging system for imaging structures of tissue, comprising
    an acoustic coupling media for acoustically coupling said tissue to an acoustic sensor array,
    an acoustic sensor array for detecting said thermoacoustic response, comprising an array of sensors arranged on a surface, and
    a source of electromagnetic radiation for irradiating said tissue to stimulate a thermoacoustic response, comprising a plurality of sources arranged about said tissue and producing synchronized electromagnetic radiation in varying polarizations or phases to irradiate said tissue with electromagnetic radiation of a desired polarization.

2. The thermoacoustic imaging system of claim 1 wherein said plurality of sources comprise a waveguide positioned to launch electromagnetic radiation toward said tissue.

3. The thermoacoustic imaging system of claim 1 wherein said plurality of sources comprise a plurality of waveguides positioned to launch electromagnetic radiation toward said tissue, said waveguides launching electromagnetic radiation in varying polarizations or phases.

4. The thermoacoustic imaging system of claim 3 wherein said plurality of sources launch electromagnetic radiation toward said tissue with vertical and horizontal polarization.

5. The thermoacoustic imaging system of claim 3 wherein said plurality of sources launch electromagnetic radiation toward said tissue with relative phase shifts of zero and ninety degrees.

6. A handheld thermoacoustic imaging system for imaging structures of tissue, comprising a device sized to be held within the human hand, the device comprising
    a source of electromagnetic radiation for irradiating said tissue to stimulate a thermoacoustic response, and
    an acoustic sensor array for detecting said thermoacoustic response, comprising an array of sensors arranged on a surface.

* * * * *